(12) United States Patent
Moolman et al.

(10) Patent No.: US 7,641,917 B2
(45) Date of Patent: Jan. 5, 2010

(54) METHOD OF ENCAPSULATING AN ACTIVE SUBSTANCE

(75) Inventors: Francis Sean Moolman, Pretoria (ZA); Heidi Rolfes, Pretoria (ZA); Thilo Lothar Van Der Merwe, Brakpan (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 10/479,783

(22) PCT Filed: May 28, 2002

(86) PCT No.: PCT/IB02/01853

§ 371 (c)(1),
(2), (4) Date: Sep. 21, 2004

(87) PCT Pub. No.: WO03/013478

PCT Pub. Date: Feb. 20, 2003

(65) Prior Publication Data

US 2005/0112205 A1    May 26, 2005

(30) Foreign Application Priority Data

May 30, 2001    (ZA) ................................ 2001/4451

(51) Int. Cl.
*A61K 9/14* (2006.01)
*A01N 25/08* (2006.01)
(52) U.S. Cl. ........................ 424/486; 424/409; 424/484; 424/489
(58) Field of Classification Search .................. 424/497, 424/400, 450, 489, 486, 409, 484
See application file for complete search history.

(56) References Cited

U.S. PATENT DOCUMENTS

| | | | |
|---|---|---|---|
| 5,027,742 A * | 7/1991 | Lee et al. ..................... | 118/300 |
| 5,766,637 A * | 6/1998 | Shine et al. .................. | 424/497 |
| 5,939,485 A * | 8/1999 | Bromberg et al. ........... | 524/556 |
| 6,087,003 A * | 7/2000 | Benoit et al. ................ | 428/403 |
| 6,183,783 B1 | 2/2001 | Benoit et al. | |
| 6,221,399 B1 * | 4/2001 | Rolfes et al. ................ | 424/489 |
| 6,350,786 B1 * | 2/2002 | Albano et al. ............ | 514/772.4 |
| 6,372,259 B1 * | 4/2002 | Kumar ........................ | 424/497 |
| 6,521,258 B1 * | 2/2003 | Mandel et al. .............. | 424/484 |

FOREIGN PATENT DOCUMENTS

| | | |
|---|---|---|
| EP | 0188309 A2 | 1/1986 |
| WO | WO 98/15348 | 4/1998 |
| WO | WO 98/51347 | 11/1998 |
| WO | WO 99/19085 | 4/1999 |
| WO | WO 99/25322 | 5/1999 |
| WO | WO 00/01373 A1 | 1/2000 |
| WO | WO 00/14145 A1 | 3/2000 |
| WO | WO 01/15664 A2 | 3/2001 |
| WO | WO 02/20624 A1 | 3/2002 |
| WO | WO 02/20645 A2 | 3/2002 |
| WO | WO 03/013478 A1 | 2/2003 |

OTHER PUBLICATIONS

Jiang et al "Interpolymer Complexation and Miscibility Enhancement by Hydrogen Bonding" Adv. Polym. Sci., vol. 146, 121-196 (1999).
Tsuchida et al "Interactions between Macromolecules in Solution and Intermacromolecular Complexes", Adv. Polym. Sci., vol. 45, 1-119 (1982).
Bekturov et al "Interpolymer Complexes" Adv. Polym. Sci., vol. 41, 99-143 (1981).
Solvent Effect on the Complex Formation of Poly(methacrylic acid) with Proton-Accepting Polymers, Hiroyuki Ohno, et al., Department of Polymer Chemistry, Waseda University, Tokyo, 160 Japan; Makromol. Chem. 181, 1227-1235 (1980).
Interpolymer Complexation and Miscibility Enhancement by Hydrogen Bonding, Ming Jiang, et al., Institute of Macromolecular Science and Laboratory of Molecular Engineering of Polymers, Fudan University, Shanghai 200433, China, Advances in Polymer Science, vol. 146, (95 pages).
Blends and Complexes of Poly(monomethyl itaconate) with Polybases Poly (N,N-dimethylacrylamide) and Poly(ethyloxazoline). Association and Thermal Behavior, Emilio Meaurio, et al., Macromolecules 1996, 29, 4598-4604.
Complexation Between Poly(styrene-co-4-vinylphenol) and Poly-(styrene-co-4-vinylpyridine) in Solution, Yubao Zhang, et al., Macromolecules 1997, 30, 6084-6089.
Interpolymer Complexes and Miscible Blends of Poly(N-vinyl-2-pyrrolidone) with Novolac Resin and the Effect of Crosslinking on Related Behaviour, Zhikai Zhong & Qipeng Guo, Polymer International 41 (1996) 315-322.
Strategies for Particle Design Using Supercritical Fluid Technologies, Peter York, PSTT, vol. 2, No. 11, Nov. 1999.
Hydrogen Bonding of Methyl Alcohol-$d$ in Supercritical Carbon Dioxide and Supercritical Ethane Solutions, John L. Fulton, et al., J. Am. Chem. Soc. 1991, 113, 8327-8334.
The Production of Protein-Loaded Microparticles by Supercritical Fluid Enhanced Mixing and Spraying, Martin J. Whitaker, et al., Journal of Controlled Release, Elsevier (8 pages).
M. Rehman, B.Y. Shekunov, P. York, P. Colthrope; Solubility and Precipitation of Nicotinic Acid in Supercritical Carbon Dioxide, Journal of Pharmaceutical Sciences, vol. 90 No. 10, Oct. 2001; pp. 1570-1582.

(Continued)

*Primary Examiner*—Michael G Hartley
*Assistant Examiner*—Leah Schlientz
(74) *Attorney, Agent, or Firm*—Husch Blackwell Sanders Welsh & Katz

(57) ABSTRACT

The invention provides a method of encapsulating an active substance in an interpolymer complex, to make an encapsulated product in particulate form. The method comprises forming a mixture of a supercritical fluid, an interpolymer complex and an active substance and then causing or allowing the interpolymer complex to encapsulate the active substance. The encapsulated product is then separated from the supercritical fluid and, if necessary, the product is subjected to size reduction to ontain particles in which the active substance is encapsulated by the interpolymer complex.

10 Claims, 5 Drawing Sheets

OTHER PUBLICATIONS

Neeta Tweari and A.K. Srivastava, Complex Formation Between Pairs of Vinyl Polymers, Macromolecules, vol. 25, No. 3, Feb. 3, 1992, pp. 1013-1016.

Ruth A. Van Leer and Michael E. Paulaitis, Solubilities of Phenol and Chlorinated Phenols in Supercritical Carbon Dioxide, J. Chem. Eng. Data, 1980, 25, pp. 257-259.

B.J. Holland, J.N. Hay, The Thermal Degradation of Poly(vinyl Alcohol), Elsevier Polymyer 42 (2001) 6775-6783.

A.M. Whittfoht, Plastics Technical Dictionary, (4 pages).

Polycaprolactone, Wikipedia (2 pages), Apr. 17, 2009.

P.R. Sundararajan, Poly(vinyl Alcohol), Polymer Data Handbook, Copyright 1999 Oxford University Press, 890-909.

J.M. Dobbs, J.M. Wong, R.J. Lahiere, and K.P. Johnson, Modification of Supercritical Fluid Phase Behavior Using Polar Cosolvents, Industrial & Engineering Chemistry Research, 1987 (26)1, pp. 56-65.

Simon S.T. Ting, Stuart J. Macnaughton, David L. Tomasko, and Neil R. Foster, Solubility of Naproxen in Supercritical Carbon Dioxide with and Without Cosolvents, Ind. Eng. Chem. Res. 1993, 32, pp. 1471-1481.

\* cited by examiner

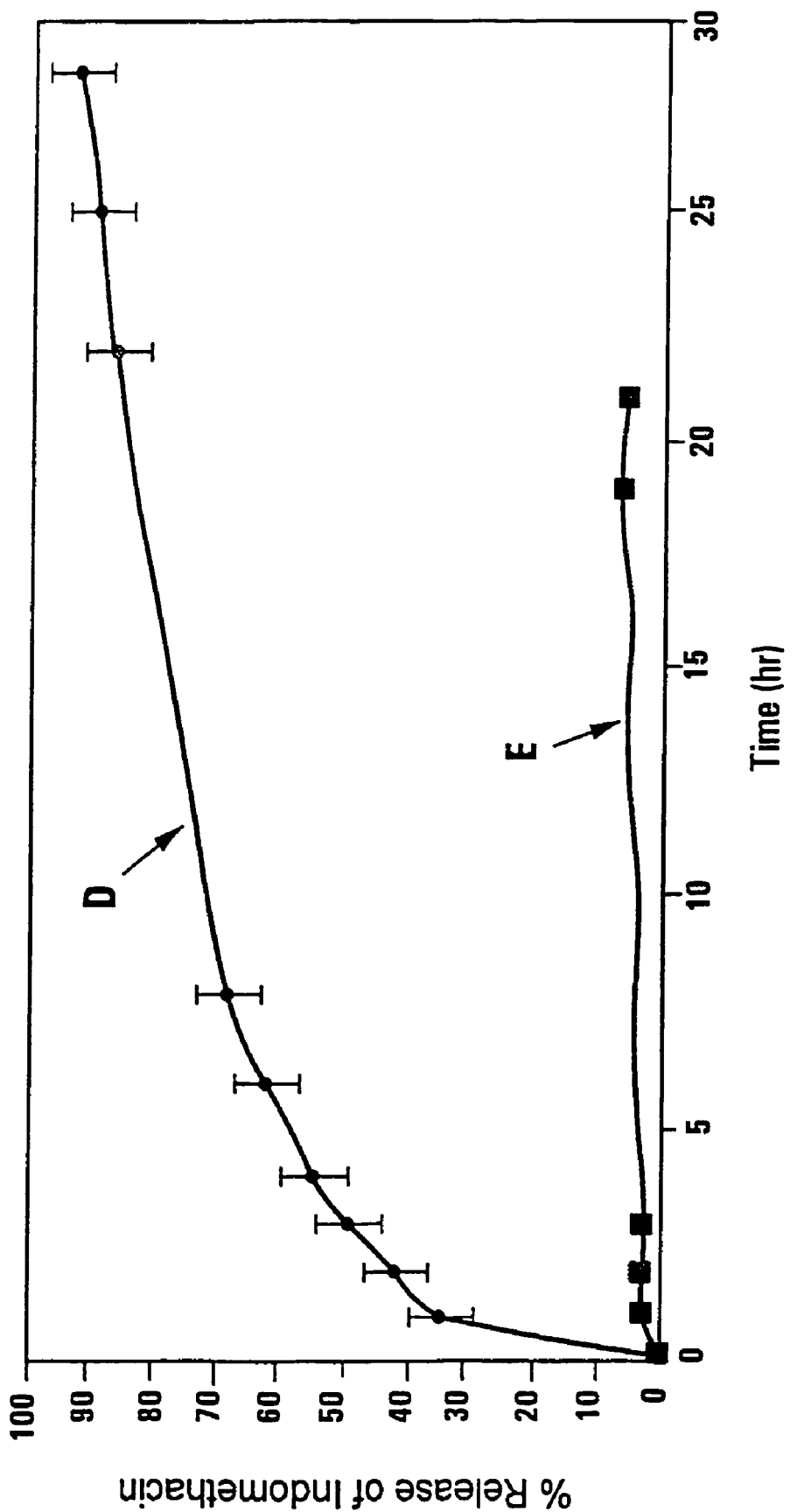

METHOD OF ENCAPSULATING AN ACTIVE SUBSTANCE

This invention relates to a method of encapsulating an active substance in an interpolymer complex to make an encapsulated product in particulate form. It also relates to such product, when made by the method.

According to the invention there is provided a method of encapsulating an active substance in a polymeric encapsulating material to make an encapsulated product in particulate form by forming a mixture of a supercritical fluid, a polymeric encapsulating material and an active substance, causing or allowing the encapsulating material to encapsulate the active substance to form an encapsulated product, separating the encapsulated product from the supercritical fluid and, if necessary, subjecting the encapsulated product to size reduction to obtain encapsulated product particles in which the active substance is encapsulated by the encapsulating material, the forming of the mixture being of the supercritical fluid, the active substance and a polymeric encapsulating material in the form of an interpolymer complex, so that the encapsulated product comprises particles of the active substance encapsulated by the interpolymer complex.

The forming of the mixture may comprise the step of dissolving a pre-prepared interpolymer complex in the supercritical fluid so that the mixture comprises a solution of the interpolymer complex as solute in the supercritical fluid as solvent.

Instead, the forming of the mixture may comprise the steps of dissolving in the supercritical fluid each of at least two complementary polymers capable of interacting together in solution in a supercritical fluid to form an interpolymer complex, to form a solution in which they are solutes and the supercritical solution is a solvent, and causing or allowing the complementary polymers to interact together to form the interpolymer complex in the supercritical fluid. In this case, if the complementary polymers interact together to form an interpolymer complex which is soluble in the supercritical fluid, the forming of the mixture may comprise the step of dissolving each of the complementary polymers in the supercritical fluid to form a solution in which the complementary polymers respectively form solutes in the supercritical fluid as solvent, the causing or allowing of the complementary polymers to interact together acting to form the interpolymer complex as solute dissolved in the supercritical fluid as solvent. Instead, if the complementary polymers interact together to form an interpolymer complex which is insoluble in the supercritical fluid, the forming of the mixture may comprise the steps of separately dissolving each of the complementary polymers in the supercritical fluid to form separate solutions in which the complementary polymers respectively form solutes in the supercritical fluid as solvent, and mixing the separate solutions together to cause or allow the complementary polymers to interact together to form the interpolymer complex, the forming of the interpolymer complex resulting in precipitation thereof from the supercritical fluid. In each case, the forming of the mixture may include the step of admixing a solubilizing agent into the mixture, the solubilizing agent acting to facilitate dissolving in the supercritical fluid of at least one member of the group consisting of the complementary polymers and the interpolymer complex. Examples of such solubilizing agents are entraining agents such as low molecular weight solvents, for example, low molecular weight alcohols, with molecular weights below 100 g/mol, which are easily soluble in the supercritical fluid and assist dissolution therein of the complementary polymers and/or of the interpolymer complex. Furthermore the forming of the mixture may comprise dispersing the active substance as a suspension of particles in the supercritical fluid, the causing or allowing of the interpolymer complex to encapsulate the particles of the active substance being by causing or allowing the interpolymer complex to precipitate from the supercritical fluid on to the surfaces of the particles.

When the interpolymer complex is soluble in the supercritical fluid and remains dissolved therein after formation thereof, the forming of the mixture of the interpolymer complex, the supercritical fluid and the active substance may include dissolving each of at least two complementary polymers capable of interacting together in solution to form an interpolymer complex, simultaneously in the same supercritical fluid, or separately to form separate complementary polymer solutions, and mixing the separate solutions together to allow the complementary polymers therein to interact to form the polymer complex in solution in the supercritical fluid. The active substance may be dispersed in at least one of the complementary solutions, before the associated polymer is dissolved therein. Instead, or in addition, the active substance may be dispersed in one of the complementary polymer solutions, after formation of the solution by dissolving its polymer in its supercritical fluid. A further possibility is that, instead or in addition, the active substance may be dispersed in the interpolymer complex solution, after the mixing of any complementary polymer solutions has taken place and after the complementary polymers have interacted to form the interpolymer complex, but before the precipitation of the interpolymer complex. In cases where the solubility of the interpolymer complex is low and the interpolymer complex is formed in the supercritical fluid at high concentrations above its saturation concentration, it may be allowed to precipitate spontaneously on to particles of the active substance as soon as the interpolymer complex is formed.

When the interpolymer complex is pre-prepared, it may be pre-prepared for example as described in the Applicant's U.S. Pat. No. 6,221,399, followed by dissolving the interpolymer complex as a solute in the supercritical fluid. In this case the active substance may be dispersed in the supercritical fluid before the interpolymer complex is dissolved therein, and/or the active substance may be dispersed in the solution, after the interpolymer complex has been dissolved in the supercritical fluid.

Causing the interpolymer complex to precipitate from the solution on to the active substance may be by any suitable method. Thus, the pressure of the supercritical fluid solvent may be altered to cause the precipitation. Similarly, the temperature of the solvent may be altered to cause the precipitation and, if desired, both pressure and temperature may be altered to cause the precipitation. Instead, or in addition, a non-solvent constituent, which causes the precipitation, may be added to the solution. A further possibility is that the solution of interpolymer complex with the active substance dispersed therein can be concentrated by allowing the solvent to evaporate, e.g. by atomizing the solution, for example in the fashion of spray drying, to produce an encapsulated product. When the active substance is a porous particulate solid the method may include precipitating the interpolymer complex on to both the outer surfaces of the particles of active substance, and on to the inner surfaces of their porous interiors.

As indicated above, forming the solution or solutions may include the use of a suitable solubilizing agent for facilitating the dissolution of one or more of the complementary polymers and/or the interpolymer complex in the supercritical fluid solvent. In this regard the supercritical fluid solvent may be a single substance or may be a mixture of a plurality of substances, i.e. a mixture of two or more different molecular species, and the method may comprise using more than one such solubilizing agent.

The interpolymer complexes of the present invention may be formed by the interaction, by interpolymer complexation, between two or more polymers by hydrogen bonding, by ionic forces, by van der Waal's forces, by hydrophobic interactions and/or by electrostatic forces, as described more fully in the Applicant's abovementioned U.S. Pat. No. 6,221,399.

The forming of the mixture may comprise, in another embodiment of the invention, the step of dissolving the active substance as solute in the supercritical fluid as solvent to form a solution of the active substance in the supercritical fluid, the causing or allowing of the interpolymer complex to encapsulate the active substance comprising atomizing the mixture in an atmosphere having a temperature and pressure such that the supercritical fluid solvent evaporates to leave a residue comprising particles in which the active substance is encapsulated by the interpolymer complex.

In this context the word evaporate naturally does not have its usual meaning of leaving the liquid state and entering the gaseous state but means, instead, that it leaves, the supercritical state and enters a subcritical state in which either the temperature is below the critical temperature, or the pressure is below the critical pressure, or both.

A further possibility is that the forming of the mixture may comprise the step of dissolving the supercritical fluid in the interpolymer complex to liquefy or plasticise the interpolymer complex. In this case, the forming of the mixture may comprise the steps of blending at least two complementary polymers, capable of interacting together when blended and in liquefied or plasticised form, to obtain a blend comprising the polymers, dissolving the supercritical fluid in the polymers, and causing or allowing the polymers to interact together in blended liquefied or plasticised form to form the interpolymer complex. The blending of the polymers may be to form a particle blend comprising polymer particles having a particle size of at most 1000 µm, preferably at most 500 µm and more preferably at most 300 µm, after which the supercritical fluid is dissolved in the polymer particles. Instead, the supercritical fluid may be separately dissolved in the complementary polymers in particle form comprising particles having a particle size of at most 1000 µm, preferably at most 500 µm and more preferably at most 300 µm, after which the polymers in liquefied or plasticised form are blended to form the blend. The causing or allowing of the interpolymer complex to encapsulate the active substance may comprise atomizing the mixture in an atmosphere having a temperature and pressure such that the supercritical fluid evaporates to leave a residue comprising particles in which the active substance is encapsulated by the interpolymer complex. In this case, the dissolving of the supercritical fluid in the interpolymer complex to liquefy or plasticise the interpolymer complex may include the step of dispersing a viscosity-reducing agent in the interpolymer complex to reduce the viscosity of the interpolymer complex to facilitate the atomizing. Thus, for example, poly(ethylene glycol) may be dissolved as a viscosity reducing agent to reduce the viscosity of the liquefied or plasticised interpolymer complex. Instead, the causing or allowing of the interpolymer complex to encapsulate the active substance may comprise allowing the supercritical fluid to evaporate to leave a solid residue comprising the active substance dispersed in the interpolymer complex, and subjecting the residue to size reduction to obtain particles in which the active substance is encapsulated by the interpolymer complex.

In general, the forming of the mixture may include the step of admixing a polymer surfactant into the mixture, for example a so-called poloxamer or poly(ethylene oxide)-poly (propylene oxide)-poly(ethylene oxide) tri-block copolymers, to enhance the interaction between the complementary polymers and/or to enhance the solubility of the supercritical fluid in the complementary polymers and in the interpolymer complex. Such polymeric surfactant is usually easily liquefiable by the supercritical fluid and helps the supercritical fluid to liquefy the complementary polymers and the interpolymer complex. However, when the surfactant is soluble in the supercritical fluid, it enhances dissolution of the complementary polymers and interpolymer complex in the supercritical fluid rather than liquefaction thereof by the supercritical fluid.

It should be noted that, particularly when the interpolymer complex encapsulating the active substance in the encapsulation product is insoluble and neither liquefiable nor plasticisable in the supercritical fluid in which the complementary polymers interact to form the interpolymer complex, the encapsulation method of the present invention may be carried out more than once, the second and each subsequent encapsulation being carried out on an active substance which is contained in the encapsulated product of the previous encapsulation.

In other words, if desired, the encapsulation method of the present invention may be repeated more than once, the second and each subsequent encapsulation being carried out on an active substance which is provided by the encapsulated product of the previous encapsulation.

The polymers which form the interpolymer complex by interpolymer complexation may be selected from complementary members of the group consisting of hydrophilic polymers, hydrophobic polymers, hydrophobically modified hydrophilic polymers and hydrophilically modified hydrophobic polymers, such as alginates, alkyl- and hydroxyalkylcelluloses, carboxymethyl cellulose and its salts, carrageenan, cellulose and its derivatives, gelatin, gellan, guar gum, gum arabic, maleic acid copolymers, methacrylic acid copolymers, methyl vinyl ether/maleic anhydride copolymers, pectins, polyacrylamide, poly(acrylic acid) and its salts, poly(ethylene glycol), poly(ethylene imine), poly(ethylene oxide), poly(propylene oxide) poly(methacrylic acid), polystyrene and sulphonated polystyrene, poly(vinyl acetate), poly(vinyl alcohol), poly(vinyl amine), poly(vinyl pyrrolidone), polyvinyl sulphonic acid), starches and their derivatives, styrene maleic anhydride copolymers, crotonic acid copolymers, xanthan gum or the like, and the derivatives and copolymers thereof.

The polymers used may be pre-treated, for example by deprotonation or preprotonation thereof, or by chemical modification thereof or the like, to tailor the type and the extent of the interpolymer interactions acting to form the interpolymer complex.

The polymers used may be linear, branched, star-shaped, comb-shaped, cross-linked, grafted, or the like.

The active substances which may be encapsulated in the interpolymer complexes to form the encapsulated products of the invention may include living organisms such as bacteria, prebiotics, probiotics, spermatozoa, ova, embryos, cells, blastocysts or the like; vaccines; proteins; hormones; enzymes; pharmaceutical compositions; drugs; vitamins; minerals; trace elements; nutrients; micro-nutrients; antioxidants; radical scavengers; ultra-violet (UV) stabilizers; pigments; organic and inorganic substances; or the like. If desired, the active substances may, prior to encapsulation in the interpolymer complex, be absorbed or adsorbed in particles of porous inert solids, such as colloidal silica, carbon or the like.

As employed in this specification, supercritical fluid is a dense gas which is maintained at a temperature above its critical temperature (the critical temperature being the temperature above which it cannot be liquefied by the application of pressure alone), and at a pressure above its critical pressure (the critical pressure being the pressure required to liquefy the gas at its critical temperature). A supercritical fluid solvent may include one or more members selected from the group consisting of hydrocarbons (such as ethane, ethene, propane, pentane, cyclohexane or toluene), dimethylether, methanol, ethanol, fluorocarbons, carbon dioxide, nitrous oxide, ammonia or the like, and mixtures thereof, optionally containing one or more solubilizers, but will usually be carbon dioxide.

It will be apparent from the aforegoing that a number of particular versions of the method of the patent invention are feasible. Thus, as foreshadowed above, and when optionally using carbon dioxide (which is the preferred supercritical fluid) as the supercritical fluid, the situation can arise when the active substance is insoluble in the supercritical fluid, the complementary polymers are soluble in the supercritical fluid, and the interpolymer complex is insoluble in the supercritical fluid. In this case, the polymers can separately be dissolved in supercritical carbon dioxide to form complementary solutions, after which the complementary solutions are mixed together to form a mixture and to allow the polymers to interact to form the interpolymer complex. This interpolymer complex will automatically precipitate from the supercritical fluid. Provided the active substance is dispersed in solid particle form in the mixture from which the interpolymer complex precipitates, the interpolymer complex will precipitate on the particles to encapsulate them. The dispersal of the active substance can take place in one or more of the complementary solutions before the mixing thereof, or in the mixture, after the mixing thereof but before the precipitation of the interpolymer complex.

Instead, the complementary polymers and the interpolymer complex may all be soluble in the supercritical fluid which is once again optionally carbon dioxide. In this case, after separate, dissolving of the polymers in supercritical carbon dioxide to form the complementary solutions, the complementary solutions may be intimately mixed and then immediately atomized, under conditions of pressure and temperature at which the carbon dioxide is no longer supercritical, to cause evaporation of the carbon dioxide and precipitation of the interpolymer complex and any remaining amounts of the complementary polymers. In this case, the active substance can be either soluble or insoluble in the supercritical fluid, and may be mixed into one or more of the complementary solutions, or into the mixture of the complementary solutions, before the atomizing. If it is soluble in the supercritical fluid, particles thereof will precipitate during the atomizing and will be encapsulated by the interpolymer complex which precipitates. Naturally, if the active substance is insoluble, the interpolymer complex can simply precipitate directly on particles thereof, in response to the atomizing. Even if the interpolymer complex is sparingly soluble or arguably insoluble in the supercritical fluid, atomizing may be through a nozzle into a particle collection chamber, after rapidly mixing the complementary solutions in a mixing chamber. By atomizing immediately after the complementary solutions are mixed is meant that the atomizing must take place before the interaction between the complementary polymers has advanced to a stage when precipitation of the atomized mixture is ineffective to encapsulate the active substance. The carbon dioxide will be maintained in a supercritical state until the atomization takes place, e.g. by heating thereof under pressure, and the atomizing should take place, as indicated above, while the interaction of the complementary polymers to form the interpolymer complex is still sufficiently incomplete to allow the interpolymer complex precipitating from the atomizing mixture to encapsulate particles of the active substance therein.

A further possibility, again when using carbon dioxide in particular as the supercritical fluid, is that the active substance is insoluble in the supercritical carbon dioxide, while the complementary polymers are insoluble therein, but are liquefiable or plasticisable by dissolution therein of the supercritical carbon dioxide, and the interpolymer complex is similarly insoluble in the supercritical carbon dioxide but is liquefiable or plasticisable by dissolution therein of the supercritical carbon dioxide. In this case a dry blend of the active material and the complementary polymers, all in sufficiently finely divided particulate form, e.g. smaller than 1000 μm, preferably smaller than 500 μm, and more preferably smaller than 300 μm, can be made, the blend being exposed to supercritical carbon dioxide to liquefy or plasticise the polymers by dissolving therein, to cause or allow them to interact together to form the interpolymer complex, which complex becomes and/or remains liquefied or plasticised by carbon dioxide dissolved or dissolving therein, the liquefied polymers and interpolymer complex typically having viscosities such that the active substance is held in suspension. The suspension of active substance in liquefied or plasticised interpolymer complex can then be atomized, e.g. by means of a spray nozzle into a particle collection chamber, into an atmosphere at a temperature and pressure selected so that the supercritical carbon dioxide dissolved in the atomized interpolymer complex evaporates to leave particles of the active substance encapsulated by the interpolymer complex. If, instead, one or more of the complementary polymers is not liquefiable or plasticisable, but the interpolymer complex is liquefiable or plasticisable, a variation of this method can be used, provided that the complementary polymers are sufficiently intimately, blended in sufficiently finely divided form to interact together to form the interpolymer complex. Indeed, the method can in principle also be used even if the active substance is soluble in the supercritical carbon dioxide and/or in the complementary polymers or interpolymer complex, as it will precipitate and become encapsulated in the interpolymer complex during the atomization. Methods involving atomization of liquefied or plasticised interpolymer complex are expected to have the advantage of efficient use of pressure chamber volume, in which the supercritical carbon dioxide is contained, when mixed with the active substance, with the complementary polymers and/or with the interpolymer complex, as it can lead to the production of atomizable mixtures containing far higher concentrations of interpolymer complex and of complementary polymers in one or more of which the supercritical carbon dioxide is dissolved, than when the complementary polymers or the interpolymer complex have to be dissolved in the supercritical fluid. Naturally, for this particular method, a suitable particulate pre-prepared interpolymer complex can be used instead of starting with the complementary polymers, the pre-prepared interpolymer complex being blended with active substance, which is typically particulate, before, during or after the liquefying or plasticising of the interpolymer complex, whether or not the active substance is soluble in the supercritical carbon dioxide.

A still further possibility is when an above blend is too viscous to atomize, e.g. because the interpolymer complex formed is insoluble in and not liquefiable or plasticisable by the supercritical carbon dioxide, the complementary polymers however being insoluble in, but liquefiable or plasticisable by, the supercritical carbon dioxide, and the active substance being either soluble or insoluble in the supercritical carbon dioxide in the polymers and/or in the complex. In this case, after the complementary polymers have interacted to form the interpolymer complex, if a pre-prepared interpolymer complex is not used instead, the liquefied or plasticised interpolymer complex, blended with the active substance, can have the pressure and temperature of its environment reduced sufficiently to allow evaporation of the supercritical carbon dioxide, to leave a solid residue of interpolymer complex with active substance dispersed therein, which can be subjected to size reduction, e.g. by milling, to produce the active substance encapsulated in the interpolymer complex as a product.

A still further possibility for the method, when the interpolymer complex is insoluble in the supercritical fluid such as carbon dioxide, if for the particulate complementary polymers to be liquefied or plasticised separately with supercritical carbon dioxide, the complementary polymers then being mixed and atomized, e.g by injecting them into a mixing chamber leading through a spray nozzle to a collecting chamber, interaction of the polymers to form the interpolymer complex taking place before evaporation of the carbon dioxide. Naturally, the atomization will take place at a temperature and pressure at which the carbon dioxide is not supercritical. While this version of the method can be used in principle whether the active substance is soluble or insoluble in supercritical carbon dioxide, being dissolved in one or more of the complementary polymers before or after they are liquefied or plasticised, or indeed being mixed in said particulate form with them during the mixing thereof, and while this version of the method can be used, whether or not the interpolymer complex is liquefiable or plasticisable by supercritical carbon dioxide dissolved therein, this method is expected to be particularly useful if the active substance is insoluble in the supercritical carbon dioxide, and the interpolymer complex is insoluble therein and not liquefiable thereby.

In versions of the method, when a solid residue comprising active substance dispersed in interpolymer complex is milled to obtain the particulate product, some of the active substance may be exposed at the particle surfaces by the milling, so that the active substance is not entirely encapsulated. It is expected, however, that the proportionate active substance so exposed will be negligible, compared with the proportion of active substance in the product which is indeed fully encapsulated by the interpolymer complex.

As far as process parameters are concerned, these will depend on the version of the above method used, and on the supercritical fluid used and its critical temperature and critical pressure, and suitable/acceptable or optimum parameters should be determined by routine experimentation, bearing practical and economic considerations in mind.

As indicated above, carbon dioxide is expected to be the usual supercritical fluid of choice, by virtue of its low cost, environmental acceptability, and ready availability, and by virtue of its acceptable critical temperature and critical pressure. For carbon dioxide it is expected that the method will usually be carried out at a pressure above 75 bar (1 bar is 100 kPa or 100 000 $N/m^2$, being 1.01324 atmospheres), preferably 150-500 bar and more preferably 250-400 bar. As far as temperature is concerned, the carbon dioxide will be at a temperature above the 32° C. critical temperature, for example 32-150° C., preferably 32-100° C. and more preferably 32-50° C.

For carbon dioxide in particular, but also for other supercritical fluids, the solids content of the starting mixture excluding the super critical fluid may be 0.1-80% by volume, preferably 10-70% and more preferably 20-60%, i.e. based on reactor volume. Any entraining agents used may in total form 0.01-10% by mass, preferably 0.1-5% and more preferably 0.5-2%, of the total mass of the entraining agent and the carbon dioxide supercritical fluid in the starting mixture loaded into the reactor, with similar proportions expected to be suitable for other supercritical fluids or mixtures thereof. Any viscosity-reducing agent used may form 1-90% by mass, preferably 5-70% and more preferably 10-60%, of the total mass of the active substance, the complementary polymers or pre-prepared interpolymer complexes, and the viscosity-reducing agents in the starting mixture loaded into the reactor. Similarly, any polymeric surfactants used may form 1-90% by mass, preferably 5-70% and more preferably 10-60%, of the total mass of the active substance, the complementary polymers or pre-prepared interpolymer complexes, and the polymeric surfactants in the starting mixture loaded into the reactor. Also similarly, any solubilising agents used may form 1-90% by mass, preferably 5-70% and more preferably 10-60%, of the total mass of the active substances, the complementary polymers or pre-prepared interpolymer complexes, and the solubilising agents in the starting mixture loaded into the reactor. The active substance content may in turn amount to 0.01-60% by mass, preferably 0. 1-50% and more preferably 1-40%, of the total mass of the active-substances and the complementary polymers or pre-prepared interpolymer complexes in the starting mixture loaded into the reactor.

When two complementary polymers are used, the mass ratio therebetween will depend on the nature or identity of the complementary polymers used, and on the interaction between them to form the interpolymer complex, and this mass ratio is expected to be 0.5:99.5-99.5:0.5, more usually 1:99-99:1 and typically 10:99-90:10. In other words (and the same applies when three or more complementary polymers are used), each complementary polymer may make up at least 0.5% by mass of the total mass of the complementary polymers used, preferably at least 1 % and more preferably at least 10%; and, similarly, each said complementary polymer will make up at most 99.5% of the total mass of the complementary polymers used, preferably at most 99% and typically at most 90%.

The invention will now be described, by way of non-limiting illustration, with reference to the following Examples and to the accompanying diagrammatic drawings, in which.

Figure 10:
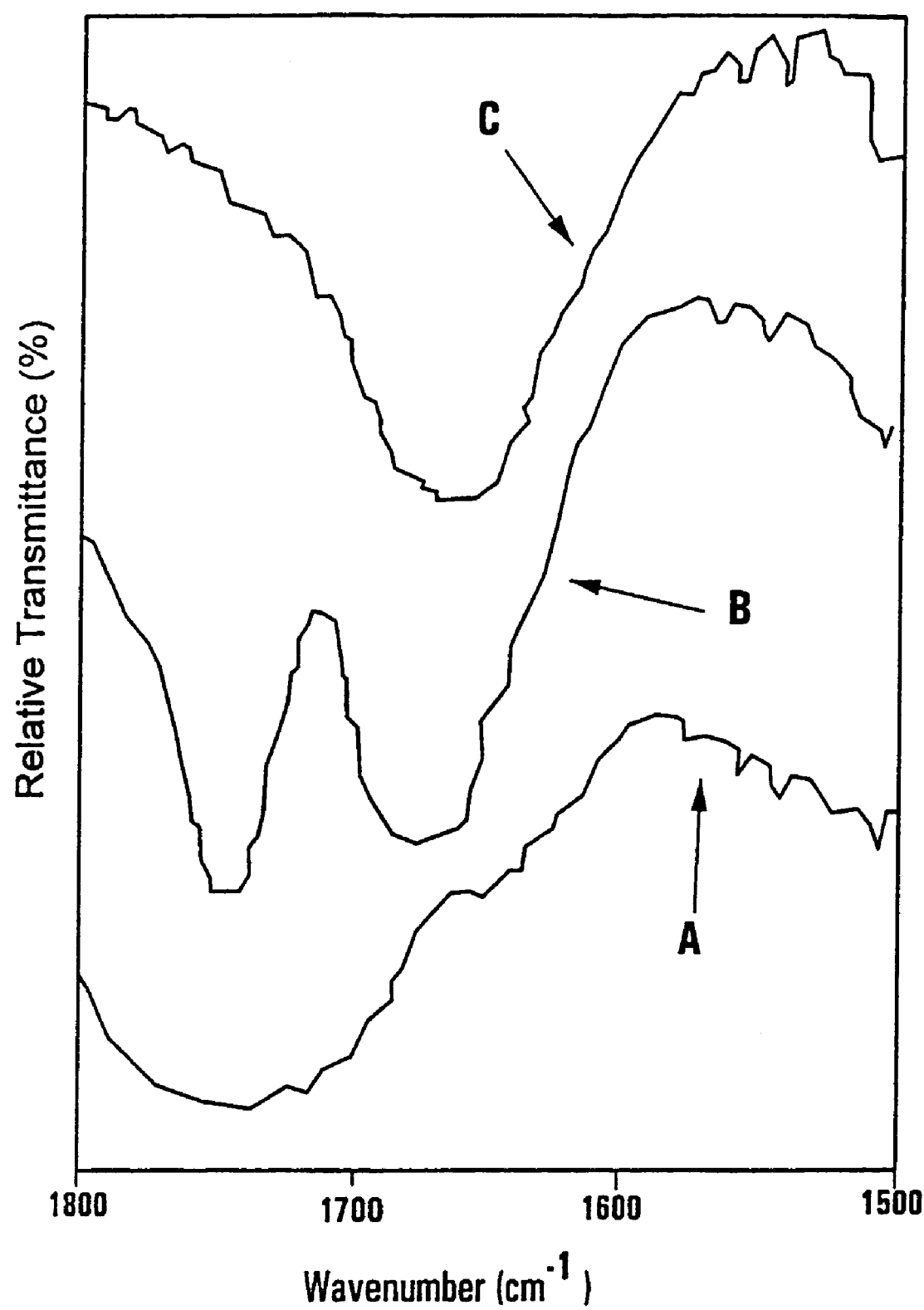

FIG. 10 shows plots of Fourier Transform infra-red spectra, respectively of two complementary polymers and of an interpolymer complex formed by interaction therebetween, in which transmittance as a percentage relative to background is plotted against wavenumber in $cm^{-1}$; and FIG. 11 shows a plot of percentage release against time of the release of an active substance encapsulated in accordance with the method of the present invention, in aqueous liquids at different pH's.

Figure 1:
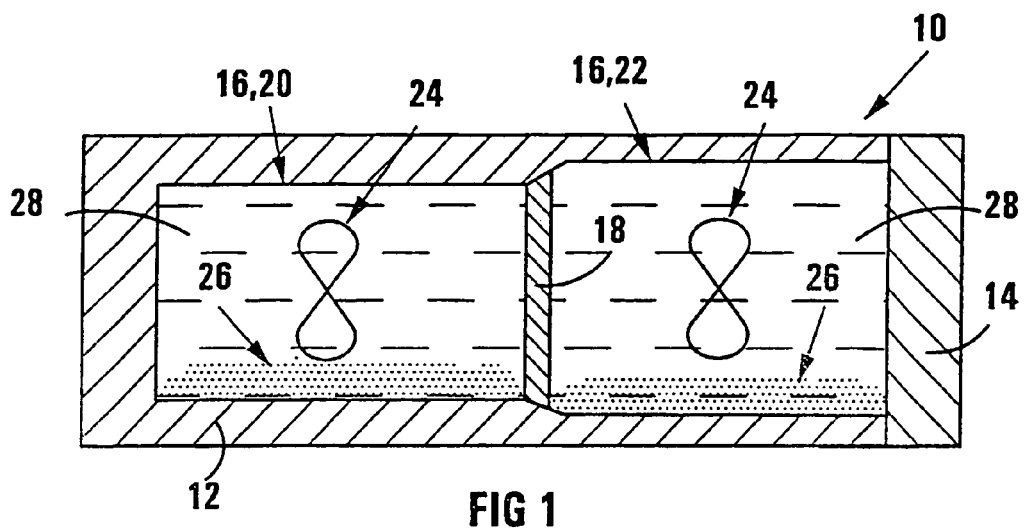
FIGS. 1-3 show, in schematic sectional side-elevation, a high pressure reactor during use thereof in accordance with the method of the present invention.
Figure 2:
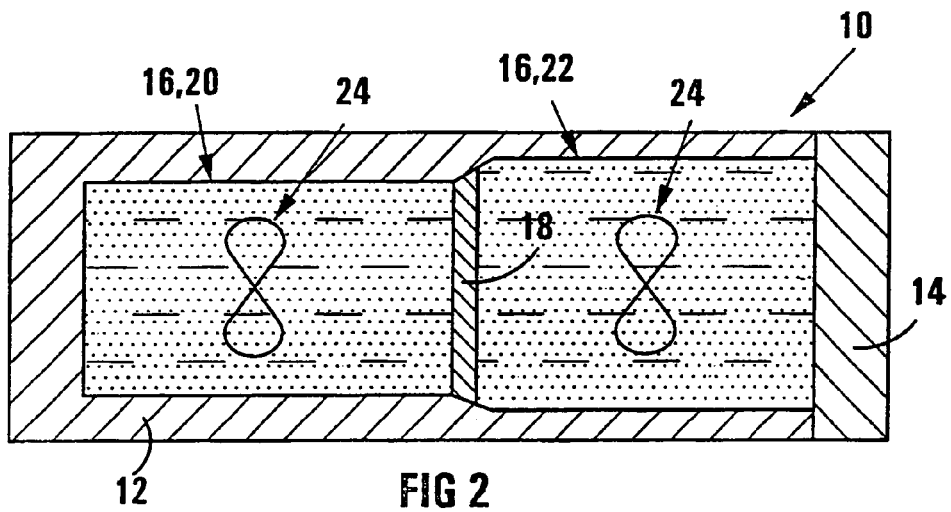
Figure 3:
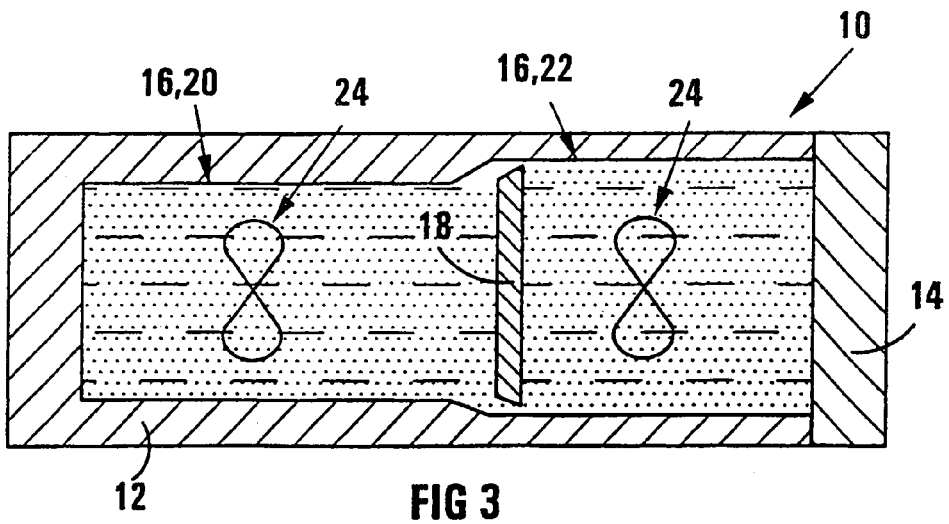

In FIGS. 1-3 of the drawings, reference numeral 10 generally designates a high-pressure reactor for carrying out the method of the present invention. The reactor 10 comprises a housing 12 provided with a closure 14. The housing has a hollow interior 16, divided by a movable partition 18 into a pair of pressure chambers 20, 22, each provided with a propeller-type stirrer 24. The chambers 20, 22 and the housing 12 are circular in cross-section, the housing 12 being axially elongated with the chambers 20, 22 co-axially and horizontally aligned with each other. The chamber 22 has a slightly larger diameter than that of the chamber 20, and the closure 14 is a lid at the end of the chamber 22 remote from the chamber 20. The partition 18 is a circular disc having a chamfered edge which seats sealingly against an internally tapered part of the wall of the housing 12, said tapered part interconnecting the chambers 20, 22. The partition 18 is axially movable between a closed position (FIGS. 1 and 2) in which it isolates the chambers 20, 22, and seals them off, from each other, and an open position (FIG. 3) in which it permits communication, and fluid flow, therebetween. The chambers 20, 22 are shown containing supercritical carbon dioxide fluid. In FIG. 1, a layer 26 of particles is shown on the lower surface of the interiors of the chambers 20-22, below supernatant supercritical carbon dioxide at 28. In FIGS. 2 and 3 particles from the layers 26 are shown dispersed and suspended in the carbon dioxide 28.

Figure 4:
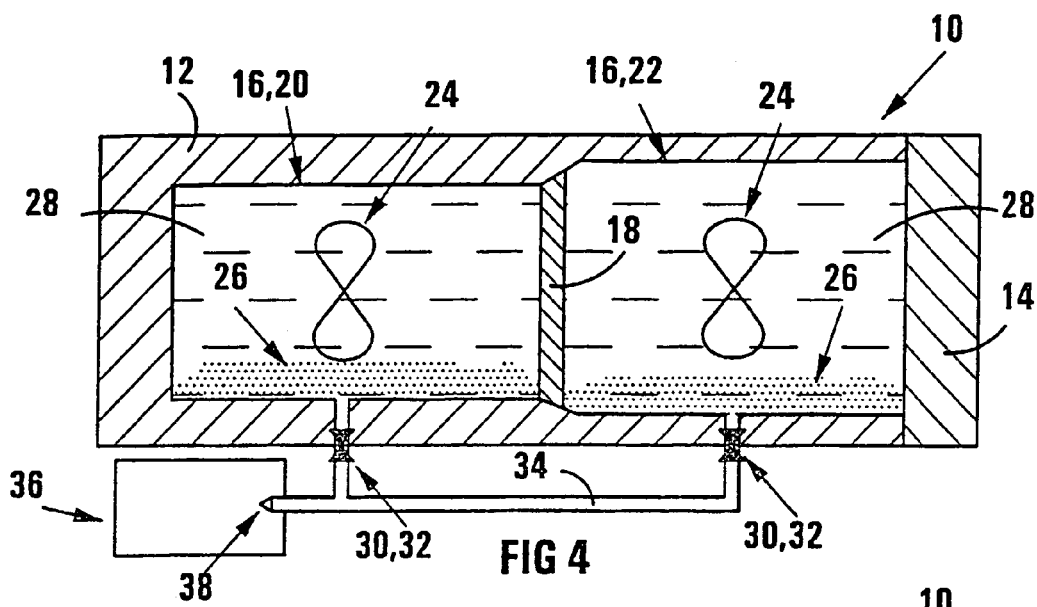
FIGS. 4-6 show, in similar schematic sectional side-elevation, a modification of the reactor of FIGS. 1-3, also during use thereof, in accordance with the method of the present invention.
Figure 5:
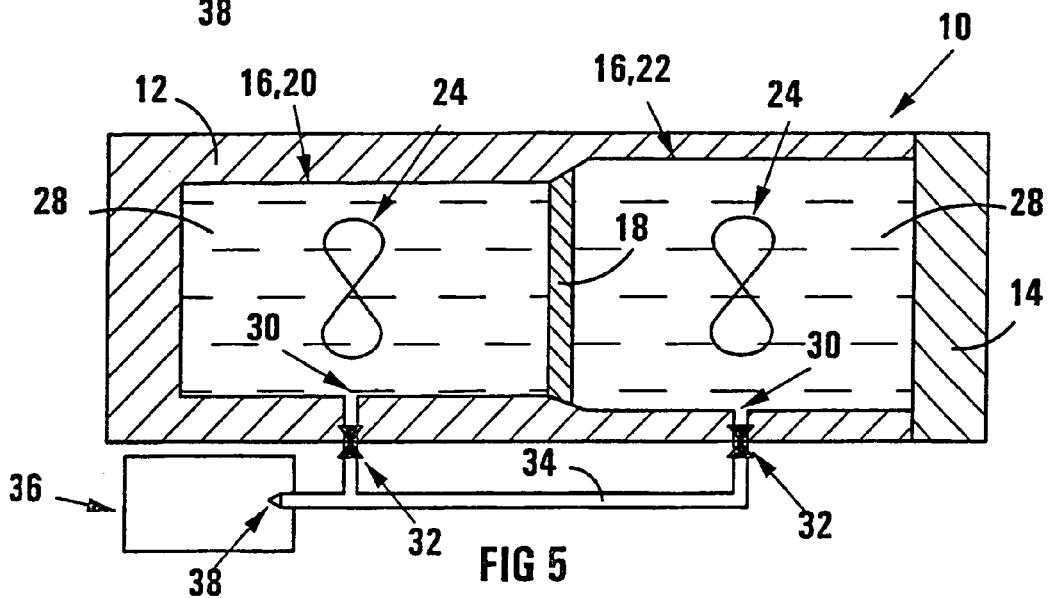
Figure 6:
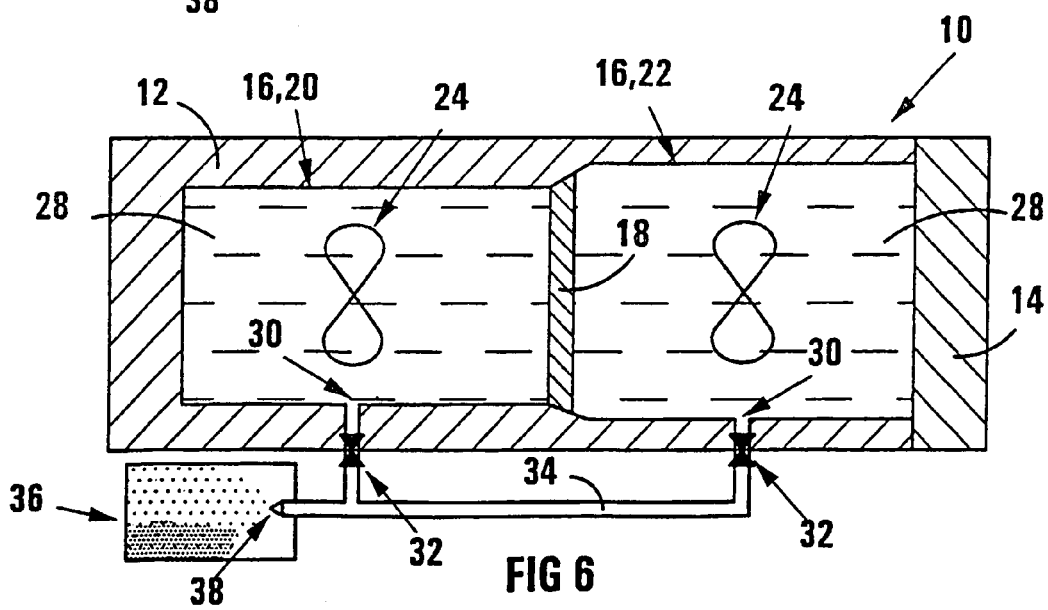

Turning to FIGS. 4-6, the same reference numerals are used to designate to the same parts as in FIGS. 1-3 unless otherwise specified. The principal difference between FIGS. 4-6 on the one hand, and FIGS. 1-3 on the other hand, is that the lower surfaces of the interiors of the chambers 20, 22 in FIGS. 4-6 are provided with fluid outlets 30 which are in turn provided with respective shut-off valves 32. The outlets 28 lead into a conduit 34 which in turn leads to a particle collection chamber defined in the hollow interior of a housing 36, into which the conduit 34 feeds via a spray-nozzle 38. No suspended particles are shown in the chambers 20, 22 of FIGS. 3 and 4, and in FIG. 4 dried and drying particles are shown in the form of a spray in the chamber 36, arising from atomized supercritical carbon dioxide entering chamber 36 via the nozzle 38 leading from the conduit 34.

Figure 7:
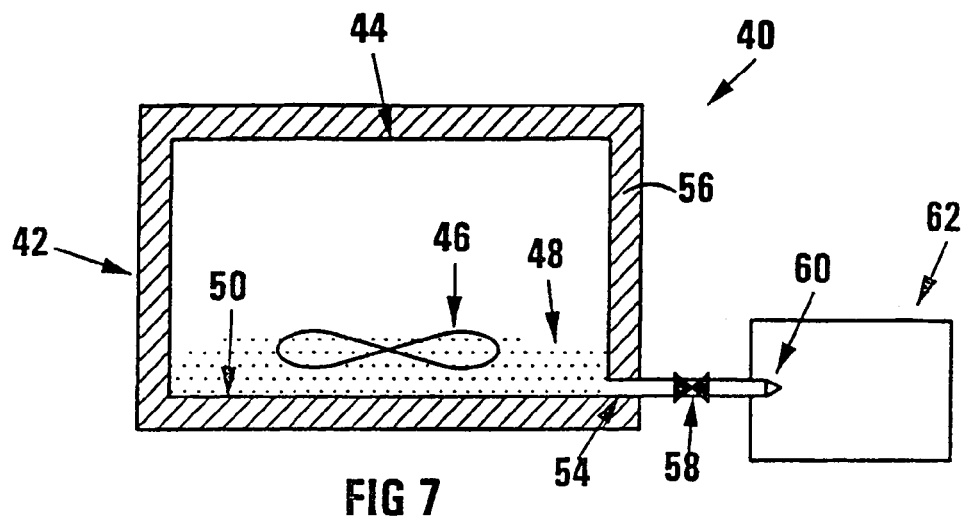
FIGS. 7-9 show, again in schematic sectional side-elevation, another high pressure reactor during use thereof in accordance with the present invention.
Figure 8:
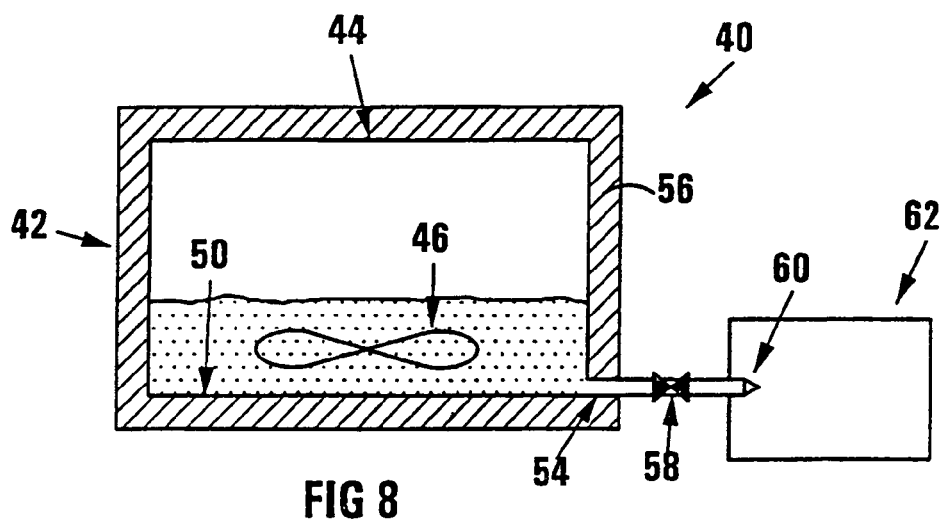
Figure 9:
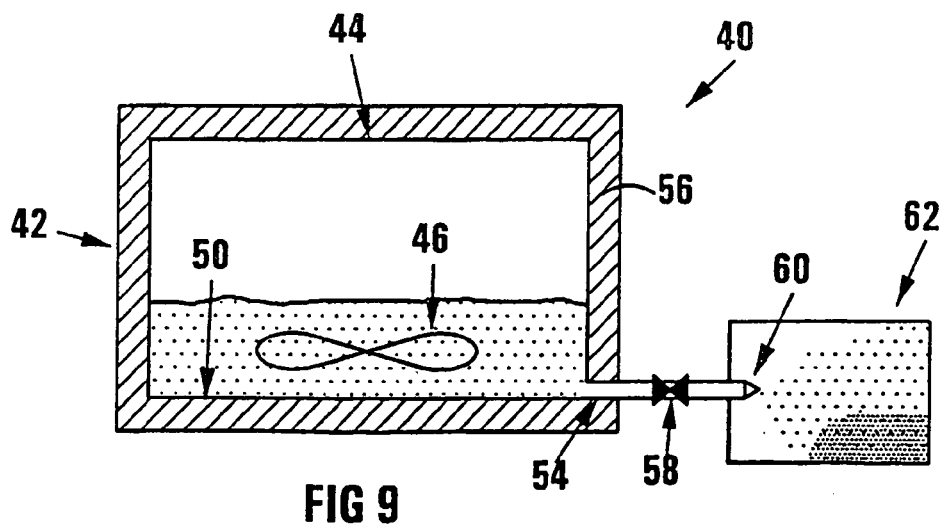

In FIGS. 7-9 a reactor generally designated 40, is shown comprising an elongated rectangular hollow housing 42 defining a single pressure chamber 44. The chamber 44 is shown containing a propeller-type stirrer 46. In FIG. 7 a layer of particles is shown at 48 on a floor 50 of the chamber 44, and in FIGS. 8 and 9 a layer 52 of liquefied or plasticised particles is shown on said floor 50. The chamber 44 is shown having a floor-level outlet 54 through an end wall 56 of the housing 42. The outlet 54 leads through a shut-off valve 58 to a spray nozzle 60 discharging into a hollow housing 62 having an interior defining a particle collection chamber. In FIG. 9 dried and drying particles are shown in the chamber 62 arising from atomized liquefied or plasticised particles from the layer 52 sprayed into the chamber 62 via the nozzle 60.

In FIG. 10 are plotted three Fourier Transform spectra, respectively designated A, B, C. Spectrum A is for a complementary polymer which is a poly(vinyl acetate)-crotonic acid copolymer, spectrum C being for a complementary polymer which is a poly(vinyl pyrrolidone), and spectrum B being for the interpolymer complex product of interaction between the said complementary polymers.

In FIG. 11 is shown a plot of the release of the active substance in question at a pH of 6.8, designated D and a plot of the release of the active substance at a pH of 1.2, designated E.

EXAMPLE 1

Interpolymer Complex
Formation—Poly(vinylacetate)-Crotonic Acid
Copolymer and Poly(vinyl Pyrrolidone)

In this example, complementary polymers in the form of 0.4 grams of poly(vinyl acetate)-crotonic acid copolymer (PVAc-CA; Aldrich) were weighed off and physically blended with 3.6 grams of poly(vinyl pyrrolidone) (PVP—Kollidon 12PF, BASF). The powder blend obtained was placed in a reactor (for example reactor 40 of FIGS. 7-9) and the reactor was sealed. The reactor was flushed with carbon dioxide for one minute.

The reactor was then pressurised with carbon dioxide from atmospheric up to a pressure of 400 bar and the temperature was raised from ambient up to 35° C. to create the desired supercritical conditions in the reactor. The blend was stirred at 2000 rpm for 2 hours to liquefy and plasticise the complementary polymers and to dissolve carbon dioxide therein. The pressure was then decreased to atmospheric pressure and the reaction product removed from the reactor. The product was found to be a monolithic piece of foamed elastic interpolymer complex. Scanning electron microscope photomicrography of the product showed it to comprise a single continuous phase. FTIR (Fourier Transform Infrared) spectroscopic measurements were carried out on the product interpolymer complex and on both the starting complementary polymers (PVP and PVAc-CA). FIG. 10 shows the respective spectra of the complementary polymers (spectra A and C) and the product interpolymer complex (spectrum B).

The PVP had a carbonyl absorption band at 1654 $cm^{-1}$ (spectrum C). The PVAc-CA had an acetate absorption band overlapping with two carbonyl stretching modes of the free and self-associated carboxylic acid groups (Zhou et al., 1998 XPS and FTi.r. Studies of Interactions in poly(carboxylic acid)/Poly(vinyl-pyridine) Complexes—Polymer 39(16) 3631-3640). This resulted in the appearance of a broad absorption band from 1700 to 1800 $cm^{-1}$ (spectrum A). This broad absorption band narrowed sharply for the product interpolymer complex (spectrum B). The PVP carbonyl absorption band at 1654 $cm^{-1}$ (spectrum C) was shifted to 1671 $cm^{-1}$ for the product interpolymer complex (spectrum B). These changes are both indications of interaction between the carboxylic acid group of the PVAc-CA and the carbonyl group of the PVP, and are characteristic of interpolymer complexes where hydrogen bonding occurs (Zhou et al., 1998, supra).

The physical characteristics of the product polymer also indicated that an interpolymer complex had been formed. First, the product polymer was elastic and tough, while both of the complementary polymers were brittle. Secondly, while PVP is highly hygroscopic, the product polymer displayed no evident hygroscopicity. Visual inspection of a physical blend of the PVP and PVAc-CA and of the product interpolymer complex after exposure to the atmosphere for 24 hours showed that the physical blend had clearly picked up moisture while the product polymer had not.

EXAMPLE 2

Interpolymer Complex Formation—PVAc-Ca and
PVP with Poly(ethyleneglycol) as Viscosity Modifier In this Example, Example 1 repeated except that 1.8 grams of poly(vinyl acetate)-crotonic acid copolymer (PVAc-CA, Aldrich) were weighed off and physically blended with 16.2 grams of poly(vinyl pyrrolidone) (PVP—Kollidon 12PF, BASF) and with 2 grams of poly(ethylene glycol) (PEG 1000, Merck), as viscosity modifier. The powder blend obtained was placed in the reactor (See 40 in FIGS. 7-9) and the reactor sealed. The reactor was flushed with carbon dioxide for one minute.

The reactor was then pressurised with carbon dioxide from atmospheric up to a pressure of 400 bar and the temperature was increased from ambient to 35° C. to create the desired supercritical conditions in the reactor. The blend was stirred at 2000 rpm for 2 hours. The pressure was then decreased to atmospheric pressure and the reactor opened. An interpolymer complex was found to have been formed in the reactor. The viscosity of the complex was found to be lower than that of the complex formed without PEG (See example 1), as indicated by the foam structure and foam distribution in the reaction chamber 44 of the reactor. The foam consisted of a single continuous phase, indicating good miscibility between the PEG, PVP and PVAc-CA.

When the interpolymer complex was sprayed through a nozzle (See 60 in FIGS. 7-9) at 275 bar, particles were formed from which a film-forming tendency of the complex was clearly discernible, as were structures formed by the rapid escape of the carbon dioxide from solution in the complex.

EXAMPLE 3

Interpolymer Complex Formation—PVP-PVAc and Poly(vinyl pyrrolidone)-Poly(vinyl acetate) Copolymer In this Example the procedures of Examples 1 and 2 were repeated except that 0.4 grams of poly(vinyl acetate)-crotonic acid copolymer (PVAc-CA, Aldrich) were weighed off and physically blended with 3.6 grams of poly(vinyl pyrrolidone)-poly(vinylacetate) copolymer (PVP-PVAc—PVP-VA S630, ISP). The blend was placed in the reactor and the reactor sealed. The reactor was flushed with carbon dioxide for one minute.

The reactor was then pressurised with carbon dioxide from atmospheric up to a pressure of 400 bar and the temperature was increased from ambient to 35° C. to create the desired supercritical conditions in the reactor. The blend was stirred at 2000 rpm for 2 hours. The pressure was then decreased to atmospheric pressure and the reactor opened. An interpolymer complex was found to have been formed in the reactor.

EXAMPLE 4

Interpolymer Complex Formation—PVAc-CA and Poly(ethylene oxide)-Poly(propylene oxide)-Poly(ethylene oxide) Tri-Block Copolymer In this Example the procedures of Examples 1-3 were repeated except that 0.4 grams of poly(vinyl acetate-crotonic acid copolymer (PVAc-CA, Aldrich) were weighed off and physically blended with 3.6 grams of poly(ethylene oxide)-poly(propylene-oxide)-poly(ethylene oxide) tri-block copolymer (PEO-PPO-PEO-Pluronic PE6800 BASF). The powder blend obtained was placed in the reactor and the -reactor sealed. The reactor was flushed with carbon dioxide for one minute.

The reactor was then pressurised with carbon dioxide from atmospheric up to a pressure of 400 bar and the temperature was increased from ambient up to 35° C. to create the desired supercritical conditions in the reactor. The blend was stirred at 2000 rpm; for 2 hours. The pressure was then decreased to atmospheric pressure and the reactor opened. An interpolymer complex was found to have been formed in the reactor.

EXAMPLE 5

Encapsulation of Insoluble Drug (Indomethacin)

In this example the following powder ingredients were physically blended:

| Ingredient | Trade Name | Supplier | Amount |
|---|---|---|---|
| poly(vinyl pyrrolidone) | Kollidon 12 PF | BASF | 7.2 g |
| poly(vinyl acetate)-crotonic acid | — | Aldrich | 0.8 g |
| Indomethacin | Indomethacin | Sigma | 2 g |

A powder blend was obtained with a maximum particle size of 500 μm, which powder blend was placed in the reactor (See 40 in FIGS. 7-9) and the reactor sealed. The reactor was flushed with carbon dioxide for one minute.

The reactor was then pressurised with carbon dioxide from atmospheric up to a pressure of 400 bar and the temperature was increased from ambient up to 35° C. to create the desired supercritical conditions in the reactor. The blend was stirred at 2000 rpm for 2 hours. The pressure was then decreased to atmospheric pressure and the reactor opened.

An interpolymer complex containing therein dispersed particles of the Indomethacin was found to have been formed in the reactor. It was removed from the reactor. The complex was then milled in a coffee grinder for 5 minutes to reduce particle size to at most about 50 μm. 2% by mass pharmaceutical grade particulate magnesium stearate (FACI,Petrow) was admixed with the milled complex as a binder. The mixture was then similarly milled for another 2 minutes to achieve uniform dispersion in the complex of the binder of similar particle size.

6 mm tablets were then pressed from the complex/binder mixture using a Manesty Type F3 Tablet Press. The tablets were used for dissolution tests in a Hanson SR-8 Dissolution Test Station. Dissolution tests were carried out at 37° C. and with stirrer speed of 75 rpm.

Determination of the Indomethacin release rate was done using UV spectrophotometry. FIG. 11 shows results of dissolution tests carried out respectively at a pH of 6.8 and at a pH of 1.2. The results are composite (average) results from eight experiments.

FIG. 11 shows controlled release of encapsulated Indomethacin drug from the tablets produced. Controlled release of the drug was achieved at a pH of 6.8, while almost no drug was released at a pH of 1.2.

EXAMPLE 6

Formation of Interpolymer Complex Before Liquefaction

In this Example 10 grams of poly(vinyl acetate)-crotonic acid copolymer(PVAc-CA, Aldrich) were weighed off and dissolved in 90 grams of ethanol heated to 50° C. Then 10 grams of poly(vinyl pyrrolidone) (PVP-Kollidon 12PF, BASF) were dissolved in 90 grams of ethanol. The two polymer solutions in ethanol were then mixed together. The ethanol was then evaporated from the mixture by heating in a vacuum oven at a temperature of about 60° C. and at a reduced absolute pressure of about 10 kPa, to obtain a solid interpolymer complex residue. This residue was then milled in a coffee grinder for 5 minutes to reduce its particle size to at most 50 µm.

Then 8 grams of the milled complex so obtained was physically blended with 2 grams of Indomethacin and further processed as described in Example 5. A similar product to that of Example 5 was obtained.

EXAMPLE 7

Addition of Polymeric Surfactant to Improve Liquefaction

The following ingredients were physically blended:

| Ingredient | Trade Name | Supplier | Amount |
| --- | --- | --- | --- |
| Poly(vinyl pyrrolidone) | Kollidon 12 PF | BASF | 7.2 g |
| Poly(vinyl acetate)-crotonic acid | — | Aldrich | 0.8 g |
| PEO-PPO-PEO copolymer | Pluronic PE6800 | BASF | 2 g |

The blending acted to produce a powder blend having a maximum particle size of 500 µm, which powder blend was placed in a reactor (40 in FIGS. 7-9) and the reactor was sealed. The reactor was then flushed with carbon dioxide for one minute.

The reactor was then pressurised with carbon dioxide from atmospheric up to a pressure of 275 bar and the temperature was increased from ambient up to 35° C., to create the desired supercritical conditions in the reactor. The blend was stirred at 2000 rpm by the stirrer to achieve liquefaction of the blend.

The liquefied blend was sprayed at a pressure of 275 bar through a 0.13 mm orifice in a spray nozzle into a collection chamber. A dry particulate product, consisting of a homogeneous blend of the interpolymer complex and the polymer surfactant, was obtained.

The full names and addresses of the suppliers of the starting materials used in the, examples are as follows:

| | |
| --- | --- |
| Aldrich | Aldrich Chemical Company<br>Post Office Box 355<br>Milwaukee<br>Wisconsin 53233<br>USA |
| BASF | BASF South Africa (Proprietary) Limited<br>Post Office Box 2801<br>Halfway House 1685<br>South Africa |
| Merck | Merck (Proprietary) Limited<br>Post Office Box 2805<br>Durban 4000<br>South Africa |
| ISP | ISP Europe<br>40 Alan Turing Road<br>Surrey Research Park<br>Guildford<br>Surrey GU2 5YF<br>England |
| Sigma | Sigma (Proprietary) Limited<br>PO Box 4853<br>Atlasville 1465<br>South Africa |

-continued

| | |
| --- | --- |
| Petrow | CJ Petrow Chemicals (Proprietary) Limited (Agents)<br>68 5$^{th}$ Avenue<br>Albertville 2193<br>South Africa |

The invention claimed is:

1. A method of encapsulating an active substance in a polymeric encapsulating material to make an encapsulated product in particulate form, the method comprising the steps of:
   forming a mixture of a supercritical fluid, a polymeric encapsulating material, and an active substance;
   causing or allowing the encapsulating material to encapsulate the active substance to form an encapsulated product;
   separating the encapsulated product from the supercritical fluid to obtain encapsulated product particles in which the active substance is encapsulated by the encapsulating material;
   wherein the supercritical fluid is carbon dioxide;
   wherein the encapsulated product comprises the active substance that has been encapsulated by an interpolymer complex;
   wherein at least two different complementary polymers of different species interact together by hydrogen bonding to form the interpolymer complex; wherein the forming of the mixture comprises the step of dissolving the supercritical fluid in the interpolymer complex to liquefy or plasticize the interpolymer complex; and wherein the polymers which form the interpolymer complex are selected from complementary members of the group consisting of poly(vinyl acetate)-crotonic acid copolymer, poly(vinyl pyrrolidone), poly(ethylene glycol), poly(vinyl pyrrolidone)-poly(vinyl acetate) copolymer and poly(ethylene oxide)-poly(propylene oxide)-poly(ethylene oxide)triblock copolymer.

2. A method as claimed in claim 1, in which the forming of the mixture comprises the steps of blending at least two complementary polymers, capable of interacting together when blended and in liquefied or plasticized form, to obtain a blend comprising the polymers, dissolving the supercritical fluid in the polymers, and causing or allowing the polymers to interact together in blended liquefied or plasticized form to form the interpolymer complex.

3. A method as claimed in claim 2, in which the blending of the polymers is to form a particle blend comprising polymer particles having a particle size of at most 1000µm, after which the supercritical fluid is dissolved in the polymer particles.

4. A method as claimed in claim 2, in which the supercritical fluid is separately dissolved in the complementary polymers in particle form comprising particles having a particle size of at most 1000 µm, after which the polymers in liquefied or plasticized form are blended to form the blend.

5. A method as claimed in claim 1, in which causing or allowing of the interpolymer complex to encapsulate the active substance comprises atomizing the mixture in an atmosphere having a temperature and pressure such that the supercritical fluid evaporates to leave a residue comprising particles in which the active substance is encapsulated by the interpolymer complex.

6. A method as claimed in claim 5, in which the dissolving of the supercritical fluid in the interpolymer complex to liquefy or plasticize the interpolymer complex includes the step of dispersing a viscosity-reducing agent in the interpolymer complex to reduce the viscosity of the interpolymer complex to facilitate the atomizing.

7. A method as claimed in claim 1, in which the causing or allowing of the interpolymer complex to encapsulate the active substance comprises allowing the supercritical fluid to evaporate to leave a solid residue comprising the active substance dispersed in the interpolymer complex, and subjecting the residue to size reduction to obtain particles in which the active substance is encapsulated by the interpolymer complex.

8. A method as claimed in claim 1, in which the forming of the mixture includes the step of admixing a polymeric surfactant into the mixture.

9. A method as claimed in claim 1, which includes subjecting the encapsulated product to size reduction to obtain encapsulated product particles.

10. A method as claimed in claim 1, in which the forming of the mixture is in the absence of a liquid.

* * * * *